United States Patent
Andrieu et al.

(10) Patent No.: US 7,927,369 B2
(45) Date of Patent: Apr. 19, 2011

(54) INTRAPARIETAL REINFORCING DEVICE FOR BIOLOGICAL CARDIAC PROSTHESIS AND REINFORCED BIOLOGICAL HEART VALVE PROSTHESIS

(75) Inventors: Raymond Andrieu, Yens (CH); Afksendiyos Kalangos, Geneva (CH)

(73) Assignee: Leman Cardiovascular SA (CH)

( * ) Notice: Subject to any disclaimer, the term of this patent is extended or adjusted under 35 U.S.C. 154(b) by 189 days.

(21) Appl. No.: 11/814,155

(22) PCT Filed: Mar. 1, 2005

(86) PCT No.: PCT/IB2005/000573
§ 371 (c)(1),
(2), (4) Date: Jul. 17, 2007

(87) PCT Pub. No.: WO2006/092648
PCT Pub. Date: Sep. 8, 2006

(65) Prior Publication Data
US 2008/0133005 A1 Jun. 5, 2008

(51) Int. Cl.
*A61F 2/24* (2006.01)
(52) U.S. Cl. .................. 623/2.14; 623/2.13; 623/2.4
(58) Field of Classification Search ........ 623/2.13–2.14, 623/2.15, 2, 2.1, 2.4
See application file for complete search history.

(56) References Cited

U.S. PATENT DOCUMENTS

| | | |
|---|---|---|
| 3,983,581 A | 10/1976 | Angell et al. |
| 4,247,292 A | 1/1981 | Angell |
| 4,345,340 A | 8/1982 | Rosen |
| 4,364,126 A | 12/1982 | Rosen et al. |
| 4,506,394 A | 3/1985 | Bedard |
| 4,535,483 A | 8/1985 | Klawitter et al. |
| 4,666,442 A | 5/1987 | Arru et al. |
| 4,692,164 A | 9/1987 | Dzemeshkevich et al. |
| 4,755,593 A | 7/1988 | Lauren |
| 4,851,000 A | 7/1989 | Gupta |

(Continued)

FOREIGN PATENT DOCUMENTS

EP 0850607 A 7/1998

(Continued)

OTHER PUBLICATIONS

U.S. Appl. No. 11/775,043, Jaffe et al.

(Continued)

*Primary Examiner* — David H Willse
*Assistant Examiner* — Seema Swaminathan
(74) *Attorney, Agent, or Firm* — Knobbe Martens Olson & Bear LLP

(57) ABSTRACT

An intraparietal reinforcing device is designed to be integrated into a biological valvular prosthesis consisting of a biological cardiac valve having a valve plane formed by leaflets attached laterally to an external wall along commissurae. The device can be placed in the organic tissue of the valve, and includes a base and a stabilizing part mounted thereon. The device can be inserted inside the external wall of the valve to reinforce the valve's structure and to maintain the valve's shape after implantation. The stabilizing part includes at least two intraparietal shafts, designed to be inserted into the valve tissue and positioned on the base so that, once the device is put in place on the valve, they are displaced laterally to the intersection point of the intersection line of the external wall with the commissurae and of the valve plane. A biological prosthesis may be provided with such a device.

23 Claims, 2 Drawing Sheets

U.S. PATENT DOCUMENTS

| | | | |
|---|---|---|---|
| 5,037,434 | A | 8/1991 | Lane |
| 5,178,633 | A | 1/1993 | Peters |
| 5,352,240 | A | 10/1994 | Ross |
| 5,549,665 | A | 8/1996 | Vesely et al. |
| 5,554,185 | A | 9/1996 | Block et al. |
| 5,595,571 | A | 1/1997 | Jaffe et al. |
| 5,713,953 | A | 2/1998 | Vallana et al. |
| 5,720,777 | A | 2/1998 | Jaffe et al. |
| 5,843,180 | A | 12/1998 | Jaffe et al. |
| 5,843,181 | A | 12/1998 | Jaffe et al. |
| 5,865,723 | A | 2/1999 | Love |
| 6,059,827 | A | 5/2000 | Fenton, Jr. |
| 6,168,614 | B1 | 1/2001 | Andersen et al. |
| 6,174,331 | B1 | 1/2001 | Moe et al. |
| 6,183,512 | B1 | 2/2001 | Howanec et al. |
| 6,383,732 | B1 | 5/2002 | Stone |
| 6,461,382 | B1 | 10/2002 | Cao |
| 6,482,228 | B1 | 11/2002 | Norred |
| 6,558,418 | B2 | 5/2003 | Carpentier et al. |
| 6,761,735 | B2 | 7/2004 | Eberhardt et al. |
| 6,767,362 | B2 | 7/2004 | Schreck |
| 7,044,966 | B2 | 5/2006 | Svanidze et al. |
| 7,172,625 | B2 | 2/2007 | Shu et al. |
| 7,247,167 | B2 | 7/2007 | Gabbay |
| 7,323,010 | B2 * | 1/2008 | Verona et al. ............... 623/2.14 |
| 7,399,315 | B2 | 7/2008 | Iobbi |
| 7,556,645 | B2 | 7/2009 | Lashinski et al. |
| 7,618,447 | B2 | 11/2009 | Case et al. |
| 2001/0039450 | A1 | 11/2001 | Pavcnik et al. |
| 2003/0023302 | A1 | 1/2003 | Moe et al. |
| 2004/0098098 | A1 | 5/2004 | McGuckin et al. |
| 2005/0075724 | A1 | 4/2005 | Svanidze et al. |
| 2005/0075726 | A1 | 4/2005 | Svanidze et al. |
| 2006/0184239 | A1 | 8/2006 | Andrieu et al. |
| 2007/0288087 | A1 | 12/2007 | Fearnot et al. |
| 2008/0243246 | A1 | 10/2008 | Ryan et al. |

FOREIGN PATENT DOCUMENTS

| | | |
|---|---|---|
| WO | WO 96/40008 A1 | 12/1996 |
| WO | WO 0067661 A | 11/2000 |
| WO | WO 01/30275 A | 5/2001 |
| WO | WO 2008/035337 A2 | 3/2008 |
| WO | WO 2008/150529 A1 | 12/2008 |

OTHER PUBLICATIONS

International Search Report for International Application No. PCT/IB2004/000707, dated Jun. 30, 2004.
International Search Report for International Application No. PCT/IB2005/000573, dated Dec. 14, 2005.
Office Action in U.S. Appl. No. 10/550,297, dated Apr. 19, 2007.
Final Office Action in U.S. Appl. No. 10/550,297, dated Nov. 20, 2007.
Office Action in U.S. Appl. No. 10/550,297 dated Apr. 17, 2008.
Amendment filed on Jul. 18, 2007 in Response to Office Action dated Apr. 19, 2007 in U.S. Appl. No. 10/550,297, filed Sep. 21, 2005.
Notice of Non-Compliant Amendment dated Jul. 27, 2007 in U.S. Appl. No. 10/550,297, filed Sep. 21, 2005.
Response filed on Aug. 8, 2007 to Notice of Non-Compliant Amendment dated Jul. 27, 2007 in U.S. Appl. No. 10/550,297, filed Sep. 21, 2005.
Supplemental Response filed on Aug. 27, 2007 to Notice of Non-Compliant Amendment dated Jul. 27, 2007 in U.S. Appl. No. 10/550,297, filed Sep. 21, 2005.
Interview Summary dated Jan. 31, 2008 in U.S. Appl. No. 10/550,297, filed Sep. 21, 2005.
Amendment Accompanying Request for Continued Examination dated Feb. 19, 2008 in Response to the Final Office Action dated Nov. 20, 2007 in U.S. Appl. No. 10/550,297, filed Sep. 21, 2009.
Amendment filed on Jul. 16, 2008 in response to Office Action dated Apr. 17, 2008 in U.S. Appl. No. 10/550,297, filed Sep. 21, 2005.
Final Office Action dated Oct. 30, 2008 in U.S. Appl. No. 10/550,297, filed Sep. 21, 2005.
Response filed on Dec. 29, 2008 to Final Office Action dated Oct. 30, 2008 in U.S. Appl. No. 10/550,297, filed Sep. 21, 2005.
Final Office Action dated Jan. 28, 2009 in U.S. Appl. No. 10/550,297, filed Sep. 21, 2005.
Response filed on Mar. 30, 2009 to Final Office Action dated Jan. 28, 2009 in U.S. Appl. No. 10/550,297, filed Sep. 21, 2005.
Interview Summary dated Apr. 2, 2009 in U.S. Appl. No. 10/550,297, filed Sep. 21, 2005.
Office Action dated Apr. 13, 2009 in U.S. Appl. No. 10/550,297, filed Sep. 21, 2005.
Interview Summary dated Jul. 7, 2009 in U.S. Appl. No. 10/550,297, filed Sep. 21, 2005.
Response filed on Jul. 13, 2009 to Office Action dated Apr. 13, 2009 in U.S. Appl. No. 10/550,297, filed Sep. 21, 2005.
Office Action dated Dec. 9, 2009 in U.S. Appl. No. 11/550,297, filed Sep. 21, 2005.
Office Action dated Dec. 31, 2009 in U.S. Appl. No. 11/755,043, filed Jul. 9, 2007.
Invitation to Pay Additional Fees and Partial International Search Report dated Feb. 11, 2010 in International Application No. PCT/US2008/069344.
Response filed on Mar. 2, 2010 in U.S. Appl. No. 11/755,043, filed Jul. 9, 2007.
Notice of Allowance dated Apr. 19, 2010 in U.S. Appl. No. 11/755,043, filed Jul. 9, 2007.
Interview Summary dated May 5, 2010 in U.S. Appl. No. 10/550,297, filed Sep. 21, 2005.
Response to Office Action filed on May 10, 2010 in U.S. Appl. No. 10/550,297, filed Sep. 21, 2005.
Notice of Allowance dated Jun. 18, 2010 in U.S. Appl. No. 11/775,043, filed Jul. 9, 2007.
Notice of Allowance dated Aug. 16, 2010 in U.S. Appl. No. 10/550,297, filed Sep. 21, 2005.

* cited by examiner

INTRAPARIETAL REINFORCING DEVICE FOR BIOLOGICAL CARDIAC PROSTHESIS AND REINFORCED BIOLOGICAL HEART VALVE PROSTHESIS

Related Applications

This application is a U.S. National Phase under 35 U.S.C. 317 of International Application PCT/IB2005/000573, filed Mar. 1, 2005, and designating the U.S., the entire disclosure of which is hereby expressly incorporated by reference.

This invention involves a reinforcing intraparietal device designed to be integrated into a biological valvular device consisting of a biological cardiac valve in which the valvular plane is formed by leaflets attached laterally to an external tubular wall along the commissurae. The device is so set up as to be placed in the organic tissue of this cardiac valve and consists of a base and a stabilizing part mounted on the base, set up to be inserted into the interior of the external tubular wall of the cardiac valve and to reinforce the structure of the latter in such a way as to maintain the form of the cardiac valve after implantation. The invention also applies to a biological valvular prosthesis fitted with such a device.

In the field of cardiac surgery involving the replacement of the heart valve, there are currently primarily artificial valvular prostheses, normally made up of a metal valve covered with synthetic tissue, and biological valvular prostheses, normally made up of a valve of animal origin prepared for implantation into the human body. These biological prostheses are subdivided into stented prostheses and non-stented prostheses.

With regard to the category of biological prostheses, the present inventors have proposed a new principle for reinforcing the biological part of the prosthesis, normally the animal-origin cardiac valve; this principle consists of inserting a reinforcing device into the interior of tissue of the cardiac valve instead of using the animal-origin valve without reinforcement in the case of non-stented prostheses or of fixing a stent to the valve surface in the case of stented prostheses. The device allowing the use of a biological prosthesis of this new type consists essentially of a short leg on which there is fixed a shaft designed to be inserted within the external tubular wall of the biological valve along the line of the intersection of this wall with the valve commissurae. This reinforcing device allows the insertion of reinforced biological valvular prostheses, bringing together the advantages of both the non-stented and stented standard biological prostheses. In essence, it allows, on the one hand, the insertion of biological prostheses having a maximum surface and thus maximum volume available for the primary function of a cardiac valve, as occurs with non-stented prostheses, by way of the space not being occupied by a large-volume device like a traditional stent. On the other hand, at the same time it allows, without recourse to a conventional stent, the stiffening and maintaining of the prostheses in their desired shape, allowing the application of a relatively simple and rapid implantation technique of currently used stented biological prostheses to this new type of reinforced biological prosthesis, by way of reinforcing the biological cardiac valve in that only one suture is required on the valvular plane in place of the two needed in the case of non-stented prostheses.

In this context, it however turns out that the insertion of the reinforcing device into the external wall of the biological valve may in certain cases cause complications. In effect, it turns out that the area around the intersection point of the joint line of the external tubular wall with the commissurae of the cardiac valve and of the valvular area of the cardiac valve of the valvular prosthesis—this point hereinafter in this document called the "marking point of the commissurae" or the "intersection point"—is marked by a particular structure of the fibres which make it up, this structure rendering the zone fragile. Insertion of a shaft in this area may cause dissection of the fibres and thus cause damage to the organic tissue in this area, which may injure the stability and the quality of the prosthesis involved and which then may constitute the beginnings of a rupture of the cardiac valve commissurae.

Moreover, since the shaft of such a reinforcing device is fixed on a relatively short leg, the implantation of a prosthesis fitted with such devices is relatively more difficult, with the result that the surgeon doing this implantation should have extensive experience.

The goal of this invention is to remove the complications mentioned above and to create a reinforcing device for biological valvular prostheses which does not cause damage to the organic tissue of the biological valve and which permits a simple and rapid implantation of the cardiac prosthesis thus obtained.

This invention concerns an intraparietal reinforcing device for biological cardiac prostheses, containing the characteristics listed in claim 1, the stabilizing part of the device being composed of at least two intraparietal shafts adapted for insertion into the organic tissue of the cardiac valve, these intraparietal shafts being positioned on the base in such a way that, once the device is in place on the cardiac valve, the shafts are displaced laterally from the point where the intersection line of the external tubular wall intersects the cardiac valve commissurae and the valvular plane of the cardiac valve of the valvular prosthesis; it also concerns biological valvular prostheses fitted with at least one such device, as listed in claim 8 and following claims.

Moreover, the device may include a base made up of a ring or a semi-ring with one part open on its circumference.

The base and/or a fastener attached to the other end of the shafts of the reinforcing devices may be covered with a biological material, such as pericardium.

This way, one gets a device which will make a biological cardiac prosthesis stable and rigid enough to retain the desired shape after implantation, all without damaging the organic tissue of the biological cardiac valve and without recourse to a conventional very large stent. At the same time, the device may be implanted, especially in the case of a circular base, by a relatively simple and rapid implantation technique, in which, when carried out with biological material covering the metal parts, the biological prosthesis shows only human biological tissue after implantation.

Other advantages follow from the characteristics expressed in the claims and in the description below, showing the invention in greater detail with the help of drawings.

The attached drawings illustrate schematically and by way of example several ways of using the invention.

The invention will now be described in detail with reference to the attached drawings.

It involves a reinforced biological valvular prosthesis adapted for placement in a heart valve. Such a cardiac prosthesis may be implanted in the sigmoidal position (aortic), the mitral position, or the tricuspid position with respect to the direction of the blood flow. The invention involves primarily intraparietal reinforcement devices necessary to implant such cardiac prostheses.

Before proceeding to the description of the intraparietal reinforcing devices and cardiac prostheses thus obtained, it is useful to describe briefly the natural structure of the human cardiac valve corresponding to that of the biological valve to be used for its replacement in order to understand the workings of the intraparietal reinforcing device and its placement in the reinforced biological valvular prosthesis.

Figure 3:
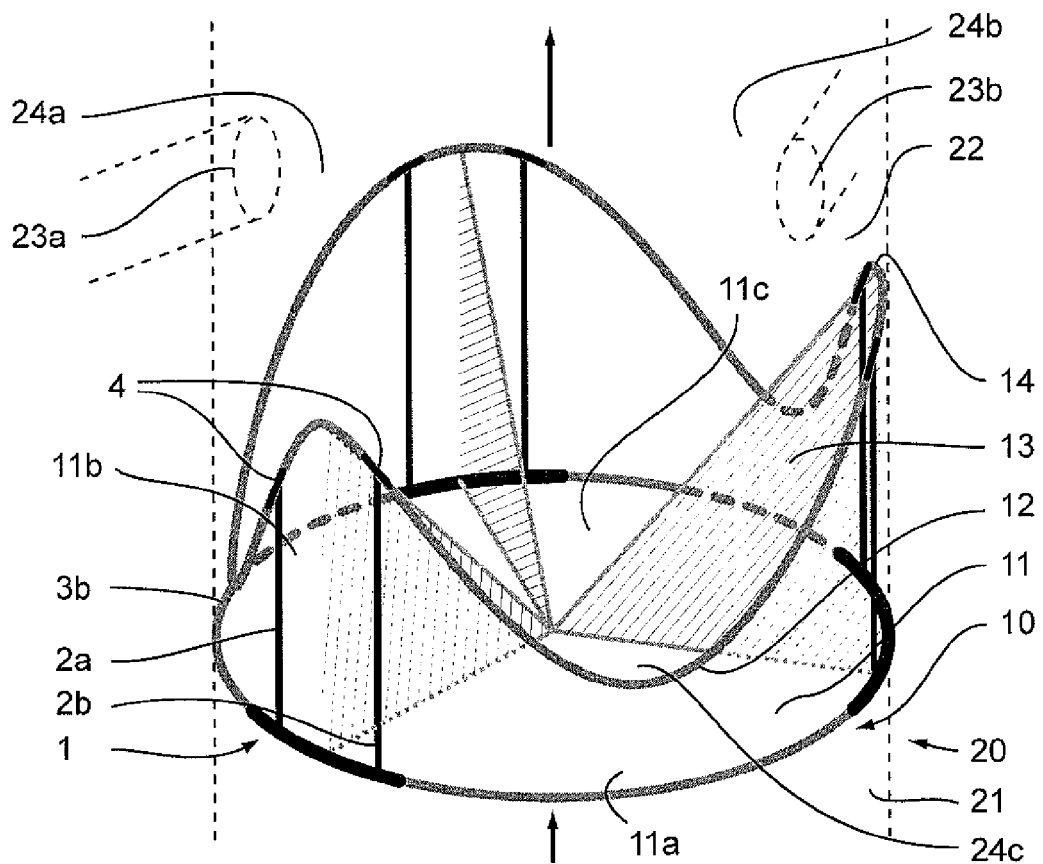
FIG. 3 shows in perspective a biological valvular prosthesis fitted with an intraparietal reinforcing device used in a fourth way, and placed, by way of example, between the aortic root and the ascending aorta.

Such a valve—for example, an animal aortic valve or even the corresponding biological cardiac prosthesis, as represented schematically in FIG. 3—is placed in the aorta 20 between the aortic root 21 and the ascending aorta 22. The cardiac valve 10 includes essentially three leaflets 11a, 11b, and 11c, forming the valvular area, and a tubular external wall 12 originally being part of the tubular wall of the animal aorta and now encircling the plane formed by the leaflets, the latter being joined to the tubular external wall 12 at their outer extremities. For leaflets 11a, 11b, and 11c, it also includes the apparently triangular vertical walls called commissurae 13, which extend to the centre of the valve or of the cardiac cavity at the mitral or tricuspid positions. These commissurae 13 are joined on one side to the two extremities of leaflets 11a, 11b, and 11c, which are oriented to the interior of the valve or of the cardiac cavity in the mitral or tricuspid positions, and on the other side, to the tubular external wall 12. Thus, the blood flow may move in the direction of the aortic root 21 toward the ascending aorta 22, or from the atrium toward the corresponding ventricular cavity, as indicated by the arrows in FIG. 3, while this is not possible in the reverse direction. The valve serving as the biological part of the reinforced biological valvular prosthesis is often removed from the animal aorta and, in the case of a replacement of the aortic valve as described in this example, the end of the tubular external wall 12 oriented in the direction of the blood flow and supporting the commissurae 13 is normally cut in a sinusoidal shape. On the one hand, this allows the integration of the sino-tubular junctions 14 corresponding to the highest contact points relative to the valvular plane, between the tubular external wall 12 and the commissurae 13, and, on the other hand, allows space to be made for the right coronary artery 23a or the left coronary artery 23b, ending around the right sinus of Valsalva 24a or the left sinus of Valsalva 24b. The part of this wall 12 opposite the non-coronary sinus of Valsalva 24c may also have a sinusoidal shape.

Figure 1A:
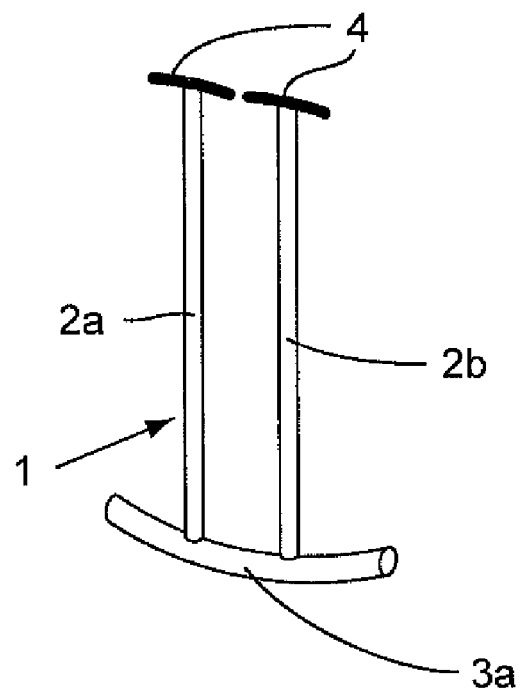
FIGS. 1a and 1b illustrate schematically the principle and two different ways of using an intraparietal reinforcing device for biological valvular prostheses.
Figure 1B:
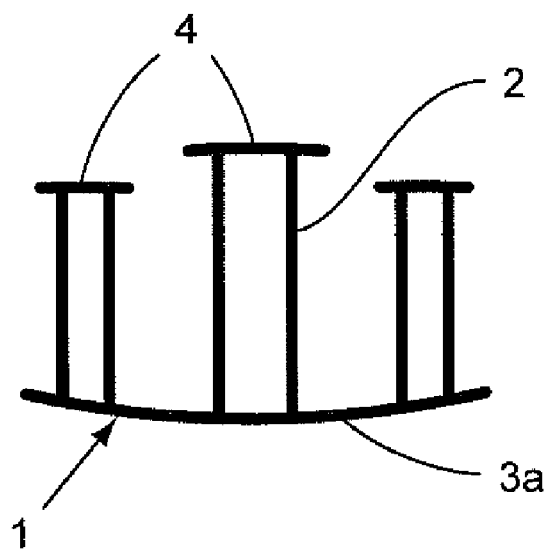

Given this natural configuration of the aortic valve and in general of the biological cardiac valves 10 used in biological cardiac prostheses, one may better understand the structure of a intraparietal reinforcing device in this invention, as shown in the example in FIGS. 1a and 1b.

In effect, FIG. 1a shows the first way of using an intraparietal reinforcing device 1 according to this invention, which is intended to be integrated into a biological valvular prosthesis consisting of a biological cardiac valve 10 having a structure as described above. This intraparietal reinforcing device 1 is meant to be placed, at least in part, within the organic tissue of this cardiac valve 10, since it is composed of a base 3 and a stabilizing part 2 mounted on the base 3. The stabilizing part 2 is designed to be inserted inside the tubular external wall 12 of the cardiac valve 10 and to reinforce the structure of the latter in such a way that it maintains the form of the cardiac valve 10 after implantation.

In order not to damage the fragile zone situated around the point where the commissurae 13 mentioned in the introduction touch it, stabilizing part 2 includes at least two intraparietal shafts 2a and 2b, designed to be inserted into the organic tissue of cardiac valve 10; these intraparietal shafts 2a and 2b are so positioned on base 3 so that, once the device is in place on the cardiac valve 10, they are displaced laterally relative to the intersection point of the intersection line of the tubular external wall 12 with the commissurae 13 of the cardiac valve 10 and the valvular plane of the cardiac valve 10 of the valvular prosthesis.

Due to this lateral movement of the intraparietal shafts 2a and 2b relative to the intersection point, the structure of the fibres in this area is not affected, resulting in better stability and better quality of the reinforced biological valvular prosthesis. For a circumference of 3 to 4 cm from the tubular external wall 12 for a cardiac valve 10 designed for an adult, the amount of lateral movement from the intersection point is at least 2 mm and may go up to half the height between the sino-tubular junctions 14 and the lowest point in the sinusoidal shape of the tubular external wall 12 between the junctions 14. In effect, outside the fragile area around the intersection point, the tubular external wall 12 shows a quite constant rigidity, and the exact placement of the intraparietal shafts 2a and 2b outside this sensitive area is chosen in a way to place the reinforcing device 1 sufficiently far from this area while guaranteeing the desired stability of the cardiac prosthesis.

Once the device 1 has been put in place on the cardiac valve 10, the intraparietal shafts 2a and 2b, which form the stabilizing part 2, are preferably positioned on the base 3 with lateral displacement identical on each side from a point on this base 3 corresponding to the intersection point. This is illustrated schematically in FIG. 1a and in FIG. 1b, which shows a second way of using a reinforcing device 1 with this invention, having more than 2 intraparietal shafts, illustrated here with six shafts 2a-2f. In contrast, the number of shafts 2 and their lateral displacement in relation to the intersection point can of course be chosen differently than the way shown in the illustrated configurations, especially in having an irregular lateral displacement. In the case of more than two intraparietal shafts 2 in particular, the placement of the shafts 2 may extend higher than the half-height cited above between the sino-tubular junctions 14 and the lowest points in the sinusoidal shape of the tubular external wall 12 between these junctions 14.

Preferably, the intraparietal shafts 2 will form a right angle with base 3. Then, once the device 1 is set in place on the cardiac valve 10 to form a reinforced valvular prosthesis, the shafts 2 will be displaced laterally and in parallel to each intersection line of the tubular external wall 12 with the commissurae 13 of the cardiac valve 10 of the valve prosthesis. Essentially, this perpendicular setup between the shafts 2 and the base 3, in which the shafts 2 are both parallel to the axis of the cardiac valve 10, simplifies the placement of the device 1 on the cardiac valve 10.

The intraparietal shafts 2 of an intraparietal reinforcing device 1 under the present invention are preferably straight. They may also have a helical shape, forming a "miniature corkscrew" where they include a helical section on their surface in order to stabilize the device 1 in the position in which it has been introduced in the tissue of the cardiac valve 10. Moreover, the intraparietal shafts 2 may include, at the other, non-fixed, end at the base 3 and in opposition to the other end which sets a fixed point on the base 3, a pointed part which is able to pierce and penetrate the organic tissue of the cardiac valve without causing damage.

The base 3 of such an intraparietal reinforcing device 1 may be made of a curved bar 3a, as illustrated in FIGS. 1a and 1b, or possibly a straight bar if the lateral displacement of the shafts 2 is not important.

Figure 2:
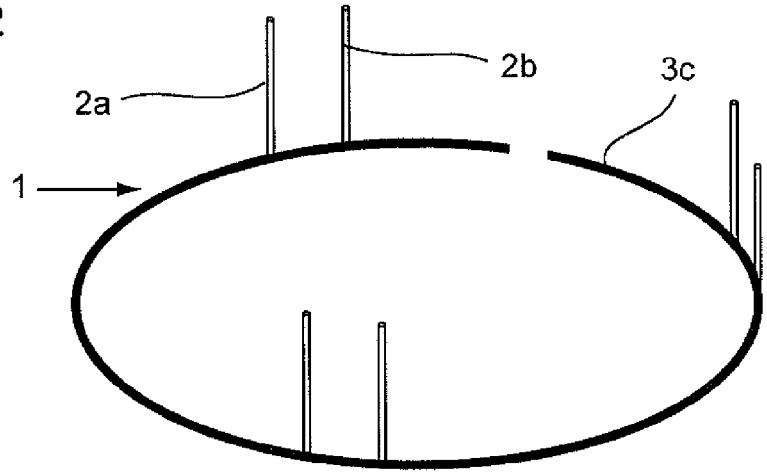
FIG. 2 shows in perspective a third way of using an intraparietal reinforcing device for biological valvular prostheses.

The base 3 may also be constructed preferably of a ring 3b—see FIG. 3—or of a semi-ring 3c, which has an open section on its circumference that allows some play in positioning on the cardiac valve 10, as illustrated in FIG. 2. In the case of a circular base 3 or a ring base 3b or a semi-ring 3c, the placement of the reinforced valvular prosthesis may be done more simply and more quickly by the transplant surgeon as a result of the rigidity of the structure of the cardiac prosthesis base.

An intraparietal reinforcing device 1 under this invention may also include at least a terminal part in the form of an attachment 4 that may be fixed on the other end of the shafts 2 in order to better secure them on the tubular external wall 12. Thus, especially in the case where the second end of a shaft 2 has a pointed part, this attachment plays the role of a cap to cover this pointed part and to guarantee the stability of the device 1 in the position in which it has been introduced into the organic tissue of the cardiac valve 10. The attachment 4 may be straight or curved, with the curvature corresponding to the curvature of the exterior circumference of the cardiac valve 10 around the site where the attachment is to be placed. For the positioning of such an attachment on the reinforcing device 1 in this invention, attachment 4 may be placed in a way visibly parallel to the base 3 or on an incline to follow the sinusoidal form of the tubular external wall 12 on its end in the direction of the blood flow. It may be fixed on a single intraparietal shaft or on several shafts 2, as illustrated in FIG. 1b.

An intraparietal reinforcing device 1 under the present invention is to be made of a material suitable for guaranteeing sufficient stability while maintaining a certain flexibility, like a flexible and/or semi-rigid and/or rigid polymer, or a flexible metal like titanium. It is produced in different sizes in order to have a set of reinforcing devices 1, allowing the fitting of biological valves 10 of corresponding size and thus having available all the sizes of cardiac prostheses required by the surgery. Moreover, the setup with a base 3 in a semi-ring 3c has additional play for the positioning of the device 1 on the cardiac valve 10.

Now that the reinforcing device 1 of this invention has been described to this point, it remains to describe in detail the composition of such a device 1 and a biological cardiac valve 10 that form a reinforced biological cardiac prosthesis according to this invention.

As noted above, FIG. 3 shows by way of example a schematic view of a biological valve prosthesis for replacement of the aortic valve 10, supplied with an intraparietal reinforcing device 1 of this invention and placed in the aorta 20 between the aortic root 21 and the ascending aorta 22.

This biological valvular prosthesis is made up of a biological cardiac valve 10 in which, in conformity with the general description above, the valvular plane is formed by leaflets 11 attached laterally to a tubular external wall 12 along the commissurae 13. The cardiac valve 10 is provided with at least one intraparietal reinforcing device 1 placed in the manner described above. It may be fitted with three devices 1 placed in the ways illustrated in FIGS. 1a and 1b, with a bar 3a as a base 3, or, in the preferred manner as illustrated in FIG. 3, with a single reinforcing device 1 with a base 3 in the form of a ring 3b (FIG. 3) or a semi-ring 3c (FIG. 2).

As for the biological part of the prosthesis, for the most part it involves a cardiac valve 10 of animal origin, especially a pig-origin aortic valve, which is then equipped with one or several intraparietal reinforcing devices 1, as determined prior to implantation.

In the biological valvular prosthesis, once the device 1 has been put in place in the cardiac valve 10, the intraparietal shafts 2 of the intraparietal reinforcing device 1 are normally inserted into the tubular external wall 12 of the biological cardiac valve in a way to be positioned parallel to the intersection lines of this wall 12 with the commissurae 13 of the cardiac valve 10.

The base 3 of a device 1 is found in the inner part of the biological prosthesis around the valvular plane, this place serving equally as an insertion point of the device 1 or of the shafts 2 into the tissue of the cardiac valve 10. The attachments 4 are placed on the other end of the shafts 2, as the case requires.

The length of a shaft 2 of the device 1 depends on the size of the aortic, mitral, or tricuspid valve to be set up and on the placement of the sinusoidal-shaped shaft along the tubular external wall 12, the length being normally between 3 mm and 30 mm. The thickness of the elements of the device is generally several tenths of a millimeter. Thus the intraparietal reinforcing devices 1 allow the biological cardiac valve 10 to be sufficiently stable to retain their form after implantation, especially the tubular external wall 12 and the area around the commissurae 13.

Preferably the base 3 and/or, as applicable, the attachment 4 of the intraparietal reinforcing device 1, are covered with a biological material like pericardium. In this case, because of the covering of the artificial parts by the pericardium or by some other suitable biological material, the biological prosthesis is not exposed after implantation except to biological tissue of the blood circulatory system and to human tissue.

Alternatively, the base 3 and/or the attachment 4 of the intraparietal reinforcing devices may be covered with tissue or a synthetic material like Teflon, Dacron, Gore-Tex, etc.

An intraparietal reinforcing device under this invention and a reinforced biological valvular prosthesis used with it may be used for the replacement of the sigmoid, mitral, or tricuspid valve of the aorta, with the space taken up by the cardiac prosthesis reinforcement reduced as much as possible because there is no use made of a conventional large stent. Thus the space reserved for blood circulation is less obstructed, something that is an important factor for the implanted patient.

In particular, such a device allows making a biological cardiac prosthesis sufficiently stable and rigid for it to retain its desired form after implantation without damaging the organic tissue of the biological cardiac valve, especially the area around the point where the commissurae come together.

Moreover, a biological valvular prosthesis reinforced by the intraparietal reinforcing devices of this invention may be designed to be implanted relatively simply and rapidly, especially in the case of a circular base, since in this case the reinforcing device shafts serve simultaneously as a mean of reinforcement and as a point of reference for the surgeon who is to do the precisely oriented operation at a location in the interior of the natural orifice, which is difficult to access.

At the same time, once the reinforced biological valvular prosthesis has been implanted, the covering of the metal parts of the cardiac prosthesis by a biological material like pericardium allows exposure of only biological tissue to the circulatory system and to human tissue.

What is claimed is:

1. Intraparietal reinforcing device designed to be integrated into a biological valvular prosthesis comprising a biological cardiac valve comprising organic tissue, in which the valve is composed of leaflets attached laterally in a natural configuration to an external tubular wall along commissurae, the external tubular wall having a thickness, the device comprising:
   a base; and
   a stabilizing part mounted on the base, the stabilizing part being designed to be inserted into the tubular external wall of the cardiac valve and designed to reinforce the structure of the cardiac valve in a way to maintain the shape of the cardiac valve after implantation, wherein the stabilizing part includes at least two intraparietal shafts designed to be inserted into the organic tissue of the cardiac valve and to extend into the thickness of the external tubular wall after insertion, the intraparietal shafts positioned on the base in a way that, once the stabilizing part is placed within the organic tissue of the cardiac valve, the shafts are displaced laterally to an intersection point of an intersection line of the tubular external wall with the commissurae of the cardiac valve and of the valvular plane of the cardiac valve of the valvular prosthesis.

2. Intraparietal reinforcing device as in claim 1, wherein once the stabilizing part is placed within the organic tissue of the cardiac valve, the intraparietal shafts are positioned on the base with a displacement identical on both sides from the point on the base corresponding to the intersection point.

3. Intraparietal reinforcing device according to claim 1, wherein the intraparietal shafts form a right angle to the base so that once the stabilizing part is placed within the organic tissue of the cardiac valve the shafts are displaced laterally relative to each intersection line of the tubular external wall with the commissurae of the cardiac valve of the valvular prosthesis.

4. Intraparietal reinforcing device according to claim 1, wherein the base is made up of a curved or straight bar.

5. Intraparietal reinforcing device according to claim 1, wherein the base is made up of a ring.

6. Intraparietal reinforcing device according to claim 1, wherein the base is made up of a semi-ring with one part open on its circumference.

7. Intraparietal reinforcing device according to claim 1, wherein said device includes at least one attachment designed to be fixed on an end of one of the shafts distal of the base.

8. Intraparietal reinforcing device according to claim 1, wherein the stabilizing part is designed to reinforce the structure of the cardiac valve in a way to maintain the shape of the cardiac valve after implantation without significantly obstructing an intraluminal volume of the cardiac valve.

9. The intraparietal reinforcing device of claim 1, wherein the intraparietal shafts are configured to reside substantially within the thickness of the external tubular wall after insertion.

10. Biological valvular prosthesis comprising a biological cardiac valve obtained from a heart, the cardiac valve having a valve plane and commissurae, in which the valve plane is formed by leaflets attached laterally in a natural configuration to a tubular external wall along the commissurae, the tubular external wall having a wall thickness, wherein said prosthesis comprises at least one intraparietal reinforcing device according to claim 1, wherein the at least one intraparietal reinforcement device extends into the wall thickness of the tubular external wall.

11. Biological valvular prosthesis according to claim 10, wherein the cardiac valve is an aortic valve of animal origin.

12. Biological valvular prosthesis according to claim 10, wherein the intraparietal shafts of the intraparietal reinforcing device are placed on the inside of the tubular external wall of the cardiac valve in parallel to the intersection lines of this device with the commissurae of the cardiac valve.

13. Biological valvular prosthesis according to claim 10, wherein the base and/or the attachment of the intraparietal reinforcing device is/are covered by biological material.

14. Biological valvular prosthesis according to claim 10, wherein the base and/or the attachment of the intraparietal reinforcing device is/are covered by synthetic material.

15. The biological valvular prosthesis of claim 10, wherein the at least one intraparietal device substantially resides within the wall thickness of the tubular external wall.

16. A bioprosthetic valve comprising:
    a cardiac valve obtained from a heart, the cardiac valve comprising a plurality of leaflets and a valve wall, the valve wall having a wall thickness, each leaflet being attached to the valve wall in a natural configuration, each leaflet being attached to an adjacent leaflet at a commissure, the commissure being attached to the valve wall at an intersection, the cardiac valve defining a circumference and a flow axis; and
    an intraparietal reinforcement inserted within the valve wall near the intersection and extending into the wall thickness, the intraparietal reinforcement comprising a first shaft and a second shaft extending generally parallel to the flow axis, the first shaft being laterally offset from the commissure in a first direction along the cardiac valve's circumference, the second shaft being laterally offset from the commissure in a second direction along the cardiac valve's circumference, the second direction being opposite the first direction.

17. The bioprosthetic valve of claim 16, wherein the first shaft and the second shaft are laterally offset from the intersection by the same distance in the first and second directions, respectively.

18. The bioprosthetic valve of claim 16, wherein the first shaft and the second shaft are each laterally offset from the intersection by at least about 2 mm.

19. The bioprosthetic valve of claim 16, further comprising a base, the intraparietal reinforcement being coupled to the base.

20. The bioprosthetic valve of claim 19, wherein the base comprises a ring.

21. The bioprosthetic valve of claim 16, further comprising an attachment member connecting the first and second shafts.

22. The bioprosthetic valve of claim 21, wherein the attachment member is a curved member.

23. The bioprosthetic valve of claim 16, wherein the intraparietal reinforcement is disposed substantially within the wall thickness.

\* \* \* \* \*

UNITED STATES PATENT AND TRADEMARK OFFICE
CERTIFICATE OF CORRECTION

PATENT NO.        : 7,927,369 B2
APPLICATION NO.   : 11/814155
DATED             : April 19, 2011
INVENTOR(S)       : Andrieu et al.

It is certified that error appears in the above-identified patent and that said Letters Patent is hereby corrected as shown below:

In Column 1, Line 9, please change "317" to --371--, therefor.

Signed and Sealed this
Fourth Day of October, 2011

David J. Kappos
*Director of the United States Patent and Trademark Office*